(12) United States Patent
Cooke et al.

(10) Patent No.: US 6,401,050 B1
(45) Date of Patent: Jun. 4, 2002

(54) NON-COMMAND, VISUAL INTERACTION SYSTEM FOR WATCHSTATIONS

(75) Inventors: John R. Cooke, Salem, CT (US); Susan S. Kirschenbaum, Kingston, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/317,087

(22) Filed: May 21, 1999

(51) Int. Cl.[7] .................................................. A61B 3/14

(52) U.S. Cl. ....................... 702/127; 702/150; 359/630; 345/7; 345/8; 345/629

(58) Field of Search ................................ 702/127, 150, 702/85, 92; 359/630, 633; 351/209, 210; 345/419, 420, 427, 848, 964, 970, 8, 7, 9, 629; 340/980

(56) References Cited

U.S. PATENT DOCUMENTS

| | | | | |
|---|---|---|---|---|
| 4,798,214 A | * | 1/1989 | Haas | 600/558 |
| 5,341,181 A | * | 8/1994 | Godard | 351/209 |
| 5,583,795 A | * | 12/1996 | Smyth | 702/150 |
| 5,590,268 A | * | 12/1996 | Doi et al | 345/848 |

* cited by examiner

*Primary Examiner*—John S. Hilten
*Assistant Examiner*—Hien Vo
(74) *Attorney, Agent, or Firm*—Michael J. McGowan; Michael F. Oglo; Prithvi C. Lall

(57) ABSTRACT

The non-command, visual interaction system provided for a shipboard watchstation has three major subsystems, an operator-locating subsystem, a visual capture subsystem, and a computer-operated watchstation. The operator-locating subsystem uses an overhead infrared tracker with location tracking hardware to identify operator presence and operator head location. An eye-tracking camera, with eye-tracking hardware monitors the watch operators visual scan, gaze location and dwell time, blink rate and pupil size. An algorithm determines when additional cueing of the operator should be made based on eye-monitoring parameters.

18 Claims, 2 Drawing Sheets

NON-COMMAND, VISUAL INTERACTION SYSTEM FOR WATCHSTATIONS

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention relates generally to the field of computer operation and in particular to eye-tracking systems and visually operated devices.

(2) Description of the Prior Art

The current viewing screens on Navy watchstations use conventional man machine interfaces (MMI) for input devices. These consist of keyboards, trackballs or mouse, touch screens, and special purpose keys and knobs (i.e. Variable Function Keys VFK). All of the current MMI input devices use haptic functions that require the operator to overtly manipulate the system. For example, to operate the viewing screen, the operator must "hook" or move a system generated cursor to a screen position and physically input the current area of interest. There is no current way for automatic sensing by the computer watchstation of what the operator is seeing.

With current research into the predictive nature of human decision making, non-invasive eye-tracking and computer intelligent agents, the non-command, non-haptic system interpretation of operator intent as actions are now feasible. Cueing of screen objects can be accomplished by the computer system based on this interpretation. The operator will only be cued to change his actions when it is needed by the system or necessary to the proper functioning of the system. Cueing of objects would not be needed if the operator is "aware" of the objects by his gazing at them with sufficient time (dwell) and frequency (scan). The use of non-invasive operator eye-tracking and pupil changes as a method of interpreting the operator's actions, attention and vigilance reduces the necessity of overt operator action with the computer workstation. The current eye-tracking devices use non-invasive camera systems to accurately project the eyes' gaze, pupil size, scan paths and object gaze dwell time. What is needed is a watchstation with the ability to interpret the operator's visual attention and location through such non-invasive devices. This non-command method will allow the tactical system to provide cueing to the operator when insufficient attention has been provided to a possible area of threat or when the system sensors detect an emergency situation.

SUMMARY OF THE INVENTION

Accordingly, it is an object of the present invention to provide a non-command, visual interaction system which has display changes and system operation based on the operator's visual attention.

Another object of the present invention is to provide a non-command, visual interaction system which monitors the operator's visual scan, gaze position, gaze dwell time, blink rate, and pupil size.

Still another object of the present invention is to provide a non-command, visual interaction system which includes a cueing algorithm to alert the operator to threats or emergencies requiring attention.

Other objects and advantages of the present invention will become more obvious hereinafter in the specification and drawings.

In accordance with the present invention, a non-command, visual interaction system is provided which comprises an operator tracking system, a visual capture system and a computer watchstation. The operator tracking comprises an overhead infrared (IR) tracker which tracks a headband-mounted source (worn by the operator), and head tracker hardware which connects to and receives data signals from the IR head tracker. The head tracker hardware provides operator presence and head location to the watchstation computer. The visual capture system comprises an eye-tracker camera and eye-tracking hardware. The eye-tracker hardware receives location data from the watchstation computer for gross aiming of the eye-tracking camera and uses camera imaging for fine resolution. Eye-data signals including visual scan, gaze position, gaze dwell time, blink rate and pupil size are captured by the eye-tracker camera and sent to the watchstation computer. An algorithm provides a sequence of steps to determine when a new object on the watchstation monitor has been seen by the operator and whether an operator cue is required.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals refer to like parts and wherein.

DESCRIPTION OF THE PREFERRED EMBODIMENT

Figure 1:
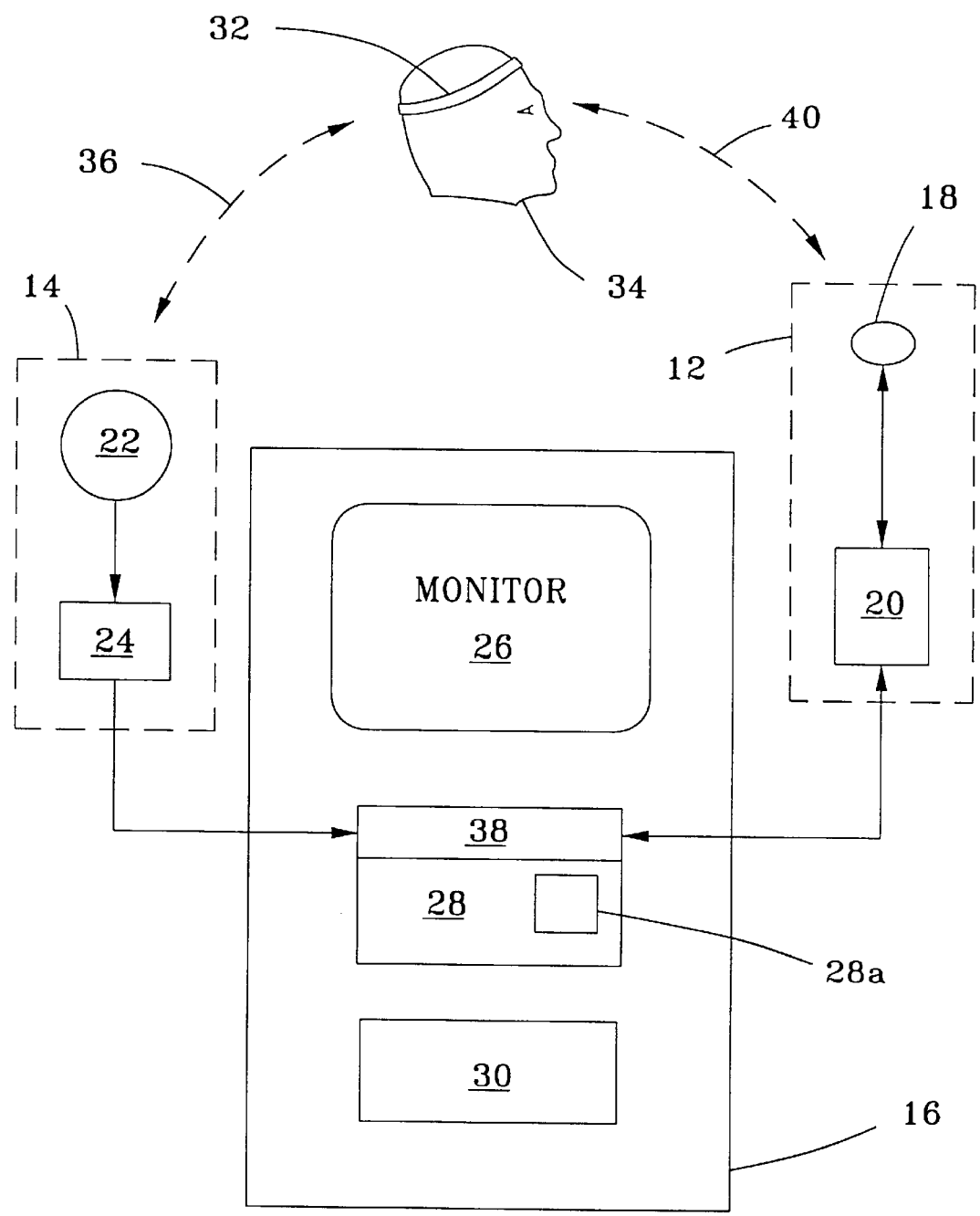
FIG. 1 is a block diagram depicting the subsystems of the non-command, visual interaction system.

Referring now to FIG. 1, the non-command, visual interaction system designated generally by the reference numeral 10, is shown with its major subsystems. The system 10 includes a visual capture subsystem 12, an operator-locating subsystem 14, both of which provide data signals to a computer watchstation 16 with a monitor 26, computer 28 and keyboard 30. The operator-locating subsystem 14 comprises a well known type of infrared tracking system comprising an overhead-mounted infrared tracker 22 which tracks a headband 32 worn by the watchstation operator 34 as indicated by dashed arrows 36. The head tracker 22 is operated by head tracker hardware 24. Data signals for the head tracker hardware are sent to the watchstation computer 28. A multichannel (MC) analog-to-digital 38 card interfaces the head tracker hardware 24 to computer 28.

The visual capture subsystem 12 comprises an eye-tracker camera 18 driven by eye-tracking hardware 20. The visual capture subsystem 12 may be any well known eye tracker system such as the model 501 system manufactured by Applied Science Laboratories of Bedford, Mass. Such systems use data signals, supplied from operator-locating subsystem 14 through watchstation computer 28, to provide gross alignment of the eye-tracker camera 18. Thereafter, the eye-tracker camera 18 uses imaging to provide the eye-tracking hardware 20 with data signal for fine alignment. As indicated by dashed arrows 40, eye-tracker camera 18 monitors operator 34 visual scan, gaze position, gaze dwell time, blink rate and pupil size for processing in computer 28 Eye-tracking hardware 20 is also interfaced with computer 28 via MC card 38.

Figure 2:
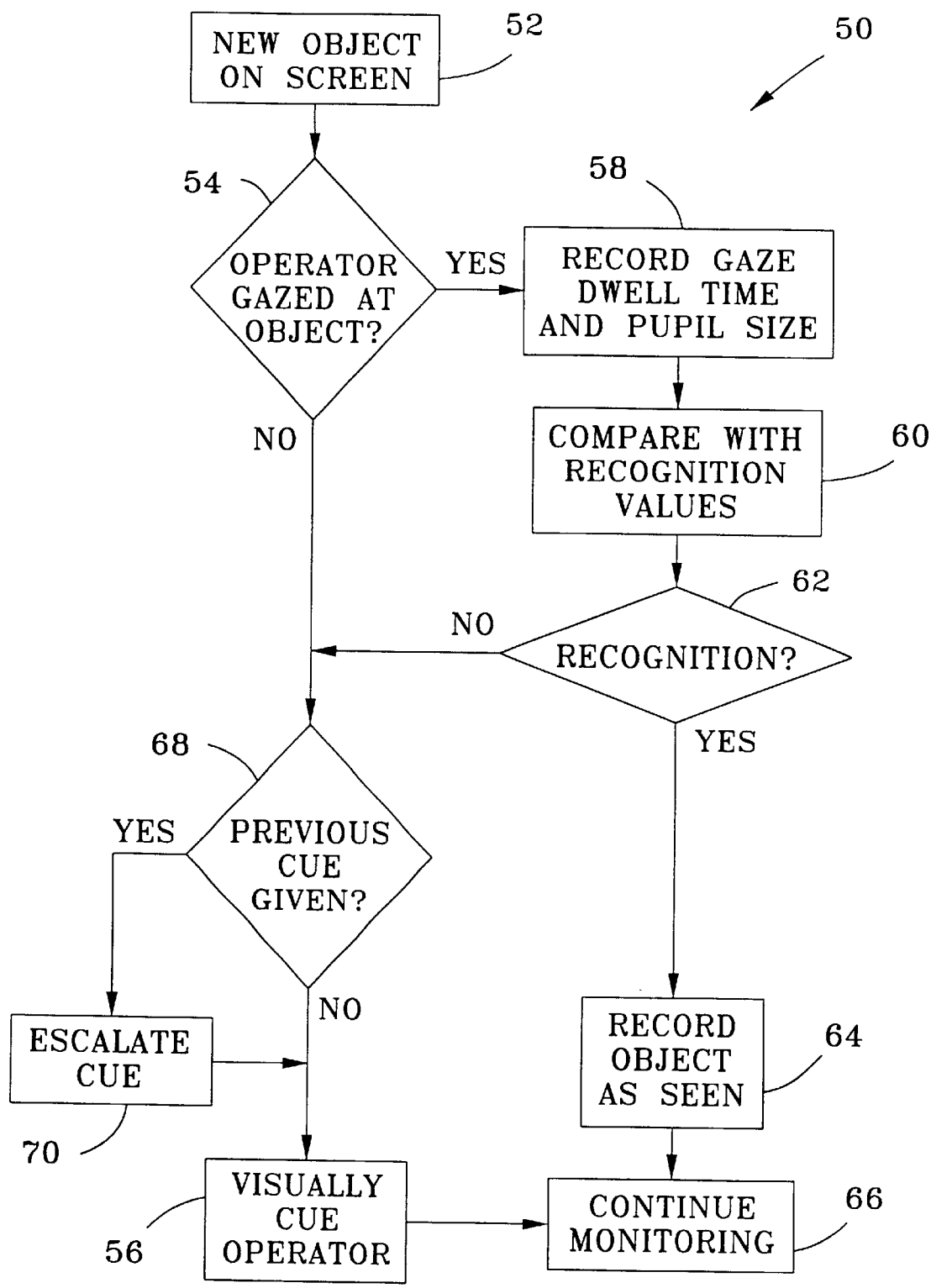
FIG. 2 is a flow chart showing the sequence of steps for providing a system cue to the operator.

Referring now also to FIG. 2, a block diagram of sequential method 50, showing the steps for initiating alerting cues to operator 34 for computer watchstation 16, is depicted. In first step 52, the watchstation computer 28 ascertains that a new object, e.g., a target, has appeared on monitor 26. The location of the new object on the screen is then processed and, in step 54, is compared to operator gaze scan and position to verify whether the operator has looked at the object. If the object has not been looked at, step 54 transfers to step 56 which generates a visual cue to the operator alerting the operator of the new object. If the operator has looked at the object, then step 54 transfers to step 58 which records operator gaze, dwell time and pupil size. The gaze, dwell time and pupil sizes are then compared at step 60 to required values for recognition. The recognition values can be input data to computer 28, or may be generated using an intelligent interpretation system, shown as block 28a within computer 28. Such intelligent interpretation systems are well known in the art and utilize neural networks to "learn" operator behavior. A true-false gate 62 then confirms whether dwell time and other operator parameters were sufficient for recognition. If not, the gate 62 branches to generate a visual cue at step 56. If gate 62 determines that recognition has occurred, the object is flagged as "seen" in step 64. System monitoring continues at step 66 after either visual cueing at step 56 or flagging at step 64. It will be noted that an object which has not been flagged at step 64 will continue to be treated as a new object, thus method 50 would continue to provide visual cues to the operator until the object is recognized. Such additional visual cues for the same object can be provided in an escalating fashion, such that the cues become stronger the longer an object is not recognized. Such escalation is shown in steps 68 and 70 where step 68 checks to see if a visual cue was previously given for the object in question and step 70 escalates the visual cue if a previous visual cue was given. The escalation may also take the form of providing an audible cue to the operator. Any additional new objects which appear while step 66 is monitoring watchstation 16 would also cause the method 50 to begin again at step 52.

The features and advantages of the present invention are numerous. The non-command, visual interaction system makes the computer watchstation aware of operator presence and aware of operator actions and intentions. By monitoring operator visual attention parameters, the computer watchstation has the capability to automatically determine if additional operator cues are required and can determine what threats or emergency situations have been overlooked. This capability is increasingly essential where one operator is monitoring a large number of display screens.

Thus, it will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A non-command, visual interaction system comprising:
   a computer;
   at least one visual display controlled by the computer;
   a visual capture subsystem connected to the computer, the capture subsystem providing operator recognition signals to the computer;
   an intelligent interpretation system within the computer using the operator recognition signals to determine cues given to the operator to prompt changes in operator recognition; and
   wherein said intelligent interpretation system is a computer process comprising the steps of:
      identifying an appearance of a new object on the at least one visual display;
      verifying operator observation of the new object;
      cueing-the operator to the new object in the event of a negative verification;
      processing operator recognition parameters in the event of a positive verification;
      comparing operator recognition parameters to preset values to confirm operator recognition of the object;
      cueing the operator to the new object in the event of a negative confirmation; and
      recording the object as observed in the event of a positive confirmation.

2. The visual interaction system of claim 1 further comprising an operator locating subsystem connected to the computer, the locating subsystem providing operator location information to the computer, the visual capture subsystem using the operator location information to align with the operator.

3. The visual interaction system of claim 2 wherein the operator locating subsystem comprises an infrared tracker detecting the presence and head location of the system operator.

4. The visual interaction system of claim 3 wherein the operator locating subsystem further comprises operator head tracker hardware.

5. The visual interaction system of claim 1 further comprising an interface card receiving the recognition signals from the visual capture subsystem and providing corresponding computer recognizable signals to the computer.

6. The visual interaction system of claim 2 further comprising an interface card receiving the recognition signals from the visual capture subsystem and the location information from the operator locating subsystem and providing corresponding computer recognizable signals to the computer.

7. The visual interaction system of claim 1 wherein said visual capture subsystem comprises an eye-tracker camera.

8. The visual interaction system of claim 7 wherein said visual capture subsystem further comprises eye-tracking hardware.

9. The visual interaction system of claim 7 further comprising an operator locating subsystem connected to the computer, the locating subsystem providing operator location information to the computer, the visual capture subsystem using the operator location information to align the eye-tracker camera with the operator.

10. The visual interaction system of claim 1 wherein the recognition signals are selected from the group consisting of operator gaze, dwell time and pupil size.

11. The visual interaction system of claim 1 wherein the cues are visual cues shown on the visual display.

12. The visual interaction system of claim 1 wherein the cueing step further comprises the steps of:
   determining if the cueing step has been performed for the object; and
   escalating the cueing in the event the cueing step has been performed for the object.

13. A method for alerting a system operator when new information is displayed by the system, the method comprising the steps of:

identifying an appearance of the new information;

verifying operator observation of the new information;

cueing the operator to the new information in the event of a negative verification;

processing operator recognition parameters in the event of a positive verification;

comparing operator recognition parameters to preset values to confirm operator recognition of the new information;

cueing the operator to the new information in the event of a negative confirmation; and recording the new information as observed in the event of a positive confirmation.

14. The method of claim 13 wherein the cueing step further comprises the steps of:

determining if the cueing step has been performed for the new information; and escalating the cueing in the event the cueing step has been performed for the new information.

15. The method of claim 13 wherein the cueing step further comprises the step of displaying a visual cue.

16. The method of claim 14 wherein the cueing step further comprises the step of displaying a visual cue.

17. The method of claim 16 wherein the escalating step further comprises the step of displaying an audible cue.

18. The method of claim 13 wherein the verifying step further comprises tracking operator recognition parameters selected from the group consisting of operator gaze, dwell time and pupil size.

* * * * *